(12) United States Patent
Chen et al.

(10) Patent No.: US 9,233,889 B2
(45) Date of Patent: Jan. 12, 2016

(54) HYDROALKYLATION PROCESSES

(75) Inventors: Tan-Jen Chen, Kingwood, TX (US); Teng Xu, Houston, TX (US); Terry E. Helton, Bethlehem, PA (US); Francisco M. Benitez, Cypress, TX (US); Charles M. Smith, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 13/640,503

(22) PCT Filed: Apr. 4, 2011

(86) PCT No.: PCT/US2011/031054
§ 371 (c)(1),
(2), (4) Date: Jan. 11, 2013

(87) PCT Pub. No.: WO2011/146167
PCT Pub. Date: Nov. 24, 2011

(65) Prior Publication Data
US 2013/0202522 A1 Aug. 8, 2013

Related U.S. Application Data

(60) Provisional application No. 61/346,590, filed on May 20, 2010.

(51) Int. Cl.
*C07C 2/74* (2006.01)
*C07C 37/08* (2006.01)
*C07C 45/53* (2006.01)

(52) U.S. Cl.
CPC . *C07C 2/74* (2013.01); *C07C 37/08* (2013.01); *C07C 45/53* (2013.01); *C07C 2101/14* (2013.01); *C07C 2521/02* (2013.01); *C07C 2523/44* (2013.01); *C07C 2529/70* (2013.01)

(58) Field of Classification Search
USPC .......................................................... 585/425
See application file for complete search history.

(56) References Cited

U.S. PATENT DOCUMENTS 3,428,696 A * 2/1969 Hallman ...................... 585/256
3,536,711 A 10/1970 Graff
(Continued)

FOREIGN PATENT DOCUMENTS

WO WO 2009021604 A1 * 2/2009
WO 2009/131769 10/2009

OTHER PUBLICATIONS

Broach, R. W., Jan, D.-Y., Lesch, D. A., Kulprathipanja, S., Roland, E. and Kleinschmit, P. 2012. Zeolites. Ullmann's Encyclopedia of Industrial Chemistry.*

(Continued)

*Primary Examiner* — In Suk Bullock
*Assistant Examiner* — Ali Z Fadhel
(74) *Attorney, Agent, or Firm* — Siwen Chen; Stephen A. Baehl (57) ABSTRACT

The invention relates to hydroalkylation processes. In the processes, a hydrogen stream comprising hydrogen and an impurity is treated to reduce the amount of the impurity in the hydrogen stream. The hydrogen is then hydroalkylated with benzene to form at least some cyclohexylbenzene. The processes also relate to treating a benzene stream comprising benzene and an impurity with an adsorbent to reduce the amount of the impurity in the benzene stream. The hydroalkylation processes described herein may be used as part of a process to make phenol.

24 Claims, 4 Drawing Sheets

(56) References Cited

U.S. PATENT DOCUMENTS

| | | | |
|---|---|---|---|
| 3,650,697 A * | 3/1972 | Goebel | 423/654 |
| 3,718,734 A * | 2/1973 | Christensen et al. | 423/228 |
| 3,926,842 A * | 12/1975 | Suggitt et al. | 502/53 |
| 3,962,362 A | 6/1976 | Suggitt | |
| 4,540,714 A * | 9/1985 | Pedersen et al. | 518/714 |
| 5,180,871 A * | 1/1993 | Matsunaga et al. | 585/400 |
| 6,037,513 A | 3/2000 | Chang et al. | |
| 7,148,389 B2 * | 12/2006 | Yang et al. | 585/250 |
| 7,906,685 B2 | 3/2011 | Chen et al. | |
| 8,084,648 B2 | 12/2011 | Buchanan et al. | |
| 2006/0219643 A1 * | 10/2006 | Wheat et al. | 210/767 |

OTHER PUBLICATIONS

Flörke, O. W., Graetsch, H. A., Brunk, F., Benda, L., Paschen, S., Bergna, H. E., Roberts, W. O., Welsh, W. A., Libanati, C., Ettlinger, M., Kerner, D., Maier, M., Meon, W., Schmoll, R., Gies, H. and Schiffmann, D. 2008. Silica. Ullmann's Encyclopedia of Industrial Chemistry.*

Augusto et al. In Effect of sulfur or nitrogen poisoning on the activity and selectivity of Y-zeolite-supported Pt—Pd catalysts in the hydrogenation of tetralin, Catalyst Letters, vol. 75, No. 1-2, 2001.*

* cited by examiner

HYDROALKYLATION PROCESSES

PRIORITY CLAIM

This application is a National Stage Application of International Application No. PCT/US2011/031054 filed Apr. 4, 2011, which claims the benefit of prior U.S. provisional application Ser. No. 61/346,590 filed May 20, 2010, both of which are hereby incorporated by reference in their entirety.

FIELD

The present invention relates to hydroalkylation processes. More particularly, the invention relates to hydroalkylation processes that include treating one or more of the reactant streams to remove impurities.

BACKGROUND

Various hydroalkylation processes are known in the art. For example, benzene and hydrogen may be contacted in the presence of a hydroalkylation catalyst to form cyclohexylbenzene. In some applications, the hydroalkylation catalyst comprises a hydrogenation metal (e.g., Pd and others) and a molecular sieve (e.g., Beta, MCM-22, MCM-49, MCM-56 and others). Other hydroalkylation catalysts may also be used.

Figure 1:
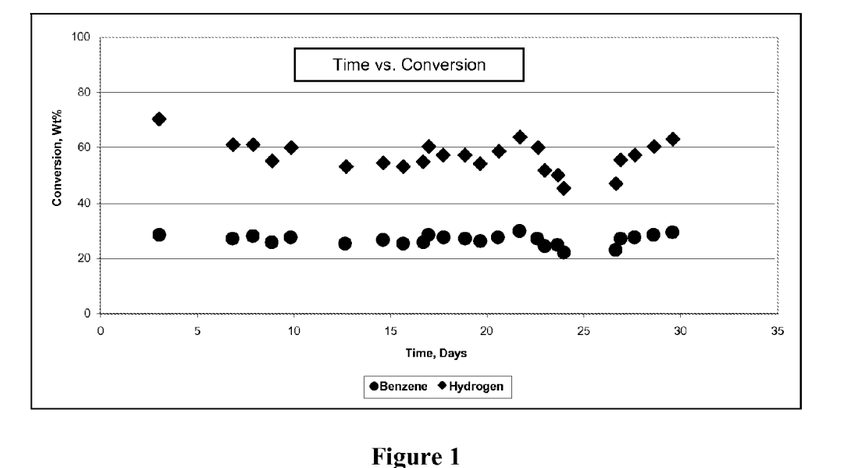
FIG. 1 shows Time vs. Conversion of hydrogen and benzene during hydroalkylation using a purified hydrogen stream and carbon monoxide-spiked hydrogen stream.
Figure 2:
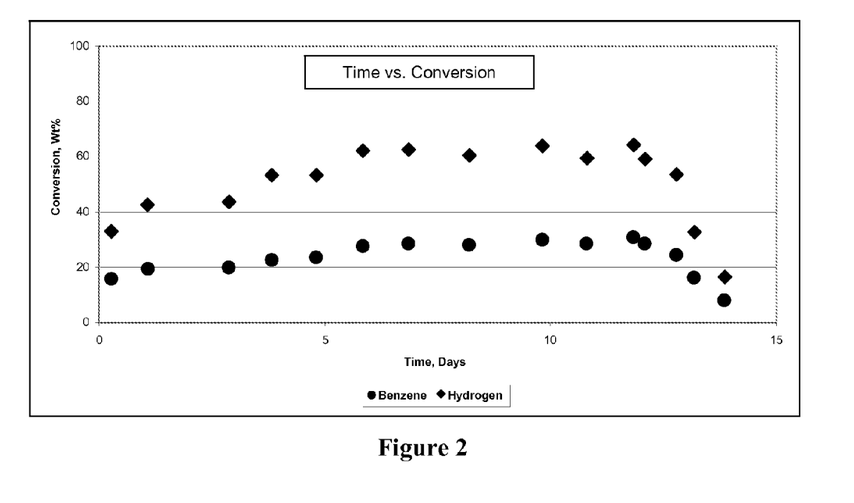
FIG. 2 shows Time vs. Conversion of hydrogen and benzene during hydroalkylation using a purified hydrogen stream and hydrogen sulfide-spiked hydrogen stream.

It has been discovered that impurities in the hydrogen and/or benzene feed streams can adversely affect the performance of the hydroalkylation catalyst. For example, and as illustrated in FIGS. 1 and 2 (with reference to Examples 1 and 2), the inventors have discovered that the presence of $CO_x$ compounds (e.g., carbon monoxide) and sulfur compounds (e.g., hydrogen sulfide and carbonyl sulfide) in the hydrogen feed stream adversely affects the performance of the hydroalkylation catalyst.

Figure 3:
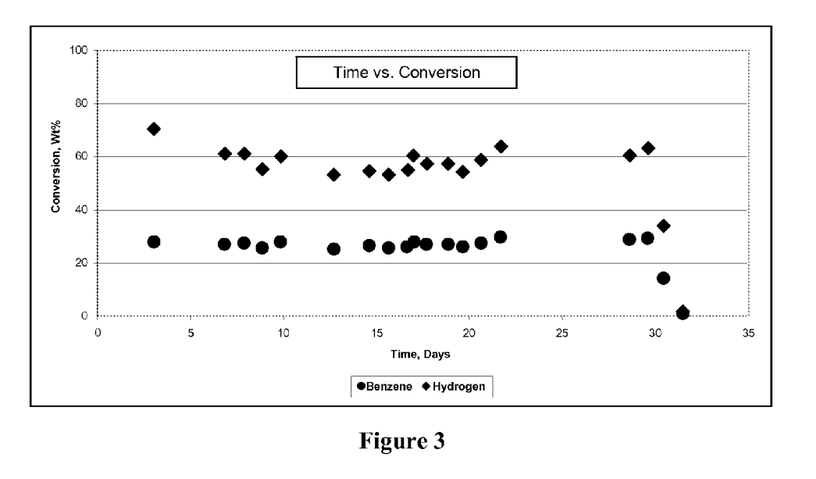
FIG. 3 shows Time vs. Conversion of hydrogen and benzene during hydroalkylation using a purified hydrogen stream and diphenylsulfide-spiked benzene stream.
Figure 4:
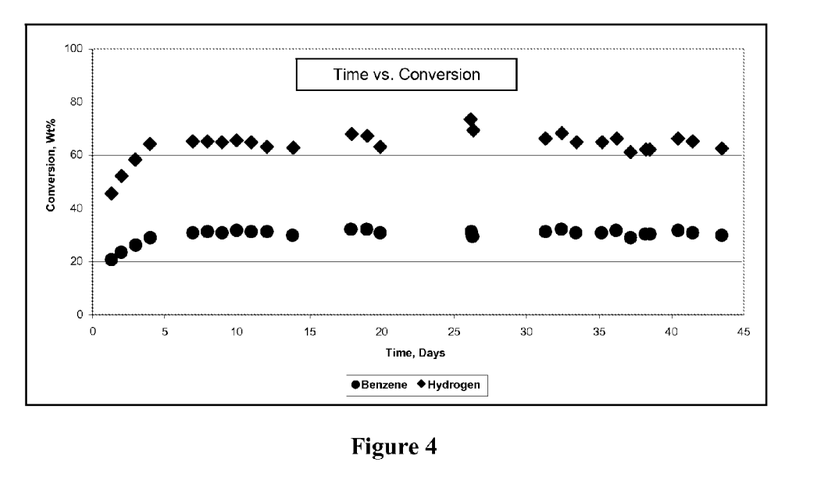
FIG. 4 shows Time vs. Conversion of hydrogen and benzene during hydroalkylation using purified benzene and hydrogen streams.

Similarly, and as illustrated in FIGS. 3 and 4 (with reference to Examples 3 and 4), the presence of sulfur compounds (e.g., diphenylsulfide) in the benzene feed adversely affects the performance of the hydroalkylation catalyst.

As such, what is needed is a process for treating hydrogen and/or benzene reactant streams to remove at least a portion of the impurities, thereby increasing the efficacy and prolonging the life of the hydroalkylation catalyst.

SUMMARY

The invention relates to a hydroalkylation process in which: (i) a hydrogen stream comprising hydrogen and an impurity is treated to reduce the amount of the impurity in the hydrogen stream; and (ii) benzene is hydroalkylated with the hydrogen to form at least some cyclohexylbenzene. In various embodiments, the impurity is one or more of carbon monoxide, carbon dioxide, and one or more sulfur compound(s) such as hydrogen sulfide and carbonyl sulfide.

The invention also relates to a hydroalkylation process in which a hydrogen stream comprising hydrogen and an impurity is treated to reduce the amount of the impurity in the hydrogen stream. In various embodiments, the treating step comprises one or more of: (i) contacting the hydrogen with a methanation catalyst under methanation conditions to convert at least some of the impurity and the hydrogen to methane and water; (ii) scrubbing the hydrogen with one or more of an amine and a caustic; and (iii) contacting the hydrogen with an adsorbent. The hydrogen may then be used to hydrogenate benzene as a first step in the hydroalkylation of benzene to form at least some cyclohexylbenzene.

The invention also relates to a hydroalkylation process in which: (a) a benzene stream comprising benzene and an impurity is contacted with one or more adsorbents to reduce the amount of the impurity in the benzene stream; and (b) the benzene is hydroalkylated with hydrogen to form at least some cyclohexylbenzene.

DETAILED DESCRIPTION OF THE EMBODIMENTS

Various specific embodiments, versions and examples of the invention will now be described, including preferred embodiments and definitions that are adopted herein for purposes of understanding the claimed invention. While the following detailed description gives specific preferred embodiments, those skilled in the art will appreciate that these embodiments are exemplary only, and that the invention can be practiced in other ways. For purposes of determining infringement, the scope of the invention will refer to any one or more of the appended claims, including their equivalents, and elements or limitations that are equivalent to those that are recited. Any reference to the "invention" may refer to one or more, but not necessarily all, of the inventions defined by the claims.

That said, described herein are hydroalkylation processes that include: (a) treating one or more reactant streams (e.g., hydrogen and/or benzene) to at least partially remove an impurity; and (b) contacting the reactant streams to form at least some cyclohexylbenzene. This process may be conducted alone, or in conjunction with one or more steps of a process to produce phenol, such as: (i) oxidation; (ii) hydroperoxide cleavage; and/or (iii) hydrogenation/dehydrogenation.

Hydrogen Treatment

As discussed above, the hydroalkylation processes described herein may comprise treating a hydrogen stream to remove one or more impurities. In accordance with various embodiments, the hydrogen reactant stream initially comprises greater than about 0.01 ppm of the impurity, or greater than 0.1 ppm, or greater than about 0.5 ppm, or greater than about 1 ppm, or greater than about 5 ppm, or greater than about 50 ppm, or greater than about 100 ppm of the impurity.

In various embodiments, the hydrogen stream is treated in one or more of the ways described herein to reduce the level of impurity to about 100 ppm or less, or about 50 ppm or less, or about 5 ppm or less, or about 1 ppm or less, or about 0.5 ppm or less, or about 0.1 ppm or less, or about 0.01 ppm or less.

The hydrogen stream may be may be supplied from any source. For example, it may be supplied from a fresh source and/or recycled from a step in a process to make phenol, e.g., the dehydrogenation of cyclohexanone to phenol.

In various embodiments, the impurity in the hydrogen stream is one or more of: (i) compounds having the general formula $CO_x$ (e.g., carbon monoxide (CO), carbon dioxide ($CO_2$), etc.); and/or (ii) sulfur-containing compounds, also referred to as "sulfur compounds" (e.g., hydrogen sulfide ($H_2S$), carbonyl sulfide (COS), diphenylsulfide, etc.).

In various embodiments, the impurity is a $CO_x$ compound and the hydrogen stream is treated by methanation. For example, the hydrogen stream (e.g., comprising the hydrogen and $CO_x$ compound) may be contacted with a methanation catalyst under methanation conditions to convert at least a portion of the $CO_x$ compound and hydrogen into methane and water. In various embodiments, the methane and/or water is removed from the hydrogen stream prior to hydroalkylation. Any conventional technique may be used to remove the methane and/or water. For example, any of a variety of adsorbents, such as 3A, 4A, 5A, and/or 13X may be used. Suitable adsorbents also include M-SG materials commercially available from SIGNA Chemistry, and/or materials commercially available from BASF under the trade name Selexsorb™. In other embodiments, the methane and/or water are not removed from the hydrogen stream prior to hydroalkylation.

The methanation catalyst may be any catalyst that facilitates methanation of the hydrogen and $CO_x$ compound. For example, the methanation catalyst may comprise one or more metal component (e.g., a Group 8-10 metal as classified by the Periodic Table of Elements, nickel, iron, nickel-iron, rare earth activated nickel oxide, rhodium and/or ruthenium) and a support. The support may comprise one or more of aluminum oxide, titania, zirconia, silica, silicate and/or aluminosilicate. Methanation catalysts are commercially available from a number of sources, such as BASF SE, SudChemie and Haldor Topsoe.

The methanation conditions may comprise a temperature of about 50° C. to about 800° C., or about 100° C. to about 700° C., or about 150° C. to about 600° C., or about 200° C. to about 500° C. and a pressure of about 1 psig (6.89 kPa, gauge) to about 400 psig (2.76 MPa, gauge), or about 10 psig (0.07 MPa, gauge) to about 350 psig (2.41 MPa, gauge), or about 15 psig (0.1 MPa, gauge) to about 300 psig (2.07 MPa, gauge).

In various embodiments, it has been discovered that one or more sulfur compounds (e.g., mercaptans and hydrogen sulfide) may be removed from the hydrogen stream by scrubbing the hydrogen stream with an amine Scrubbing may be conducted using an absorber or any other known or hereinafter devised scrubbing system or method. The amine may be one or more primary, secondary or tertiary amines having of the general formula $NR_1, R_2, R_3$:

where $R_1$, $R_2$ and $R_3$ are substituents having between 1 and 10 carbon atoms or hydrogen. Amines include monoethanol amine (MEA), diethanol amine (DEA), triethanol amine (TEA), diglycol amine (DGA), diisopropanol amine (DIPA), methyldiethanol amine (MDEA), N,N,N',N'-tetramethylpropylenediamine (TMPDA), N,N,N',N'-tetramethylbutylenediamine (TMBDA), N,N,N',N'-pentamethyldiethylenetriamine (PMDETA), N,N,N',N-tetramethylethylenediamine (TMEDA), N,N,N',N'-pentamethyldipropylenetriamine (PMDPTA), N,N'-dimethylpiperazine (DMP), 2-methylpentamethylene diamine (MPMD), bis(hexamethylene)triamine, 1,2-diaminocyclohexane, pentanediamine (DAMP), hexamethylenediamine and hexamethyleneimine, polyethyleneimine (PEI).

Additionally or alternatively, the hydrogen stream may be treated by scrubbing with a caustic to at least partially remove one or more sulfur compounds. Any caustic that at least partially removes and/or neutralizes sulfur compounds may be used. Suitable caustics include, but are not limited to, sodium hydroxide and potassium hydroxide, sodium carbonate, and solutions thereof.

Additionally or alternatively, the hydrogen stream may be passed over or through one or more absorbents to at least partially remove one or more sulfur compounds. Suitable adsorbents include, but are not limited to, activated alumina, activated carbon, zinc and copper-zinc (CuZn) materials, 3A, 4A, 5A and 13X. Suitable adsorbents also include M-SG materials commercially available from SIGNA Chemistry, and/or materials commercially available from BASF under the trade name Selexsorb™.

In various embodiments, the treated hydrogen stream contains: (i) less than 0.5 ppm of carbon monoxide, or less than 0.1 ppm of carbon monoxide; (ii) less than 100 ppm of carbon dioxide, or less than 50 ppm of carbon dioxide; and/or (iii) less than 5 ppm of sulfur, or less than 1 ppm of sulfur, or less than 0.1 ppm of sulfur.

Benzene Treatment

As discussed above, the hydroalkylation processes described herein may comprise treating a benzene reactant stream to remove one or more impurities. The benzene stream may be treated alone, or in addition to, the hydrogen stream. In accordance with various embodiments, the benzene reactant stream initially comprises greater than 0.01 ppm of the impurity, or greater than 0.1 ppm of the impurity, or greater than 0.5 ppm, or greater than 1 ppm, or greater than 50 ppm, or greater than 100 ppm of the impurity.

In various embodiments, the benzene stream is treated in one or more of the ways described herein to comprise about 100 ppm or less of the impurity, or about 50 ppm or less, or about 5 ppm or less, or about 1 ppm or less, or about 0.5 ppm or less, or about 0.1 ppm or less, or about 0.01 or less.

The benzene reactant stream may be may be supplied from any source. For example, it may be supplied from a fresh source and/or recycled from a step in the phenol production process (e.g., an alkylation or hydroalkylation step).

In various embodiments, the impurity in the benzene stream is nitrogen and/or a sulfur compound.

In various embodiments, the nitrogen and/or sulfur compound may be removed by passing the benzene stream over or through one or more adsorbents. Any adsorbent that at least partially removes nitrogen and/or sulfur compounds may be used. For example, the adsorbent may be a molecular sieve such as 3A, 4A, 5A (wherein "A" refers to the pore size of the molecular sieve in Angstroms), clay, activated alumina, amorphous silica-alumina and/or a zeolite. Suitable adsorbents also include M-SG materials commercially available from SIGNA Chemistry, and/or materials commercially available from BASF under the trade name Selexsorb™.

In various exemplary embodiments, at least two adsorbents are used. In one embodiment, two molecular sieves are used. For example, one molecular sieve may have a silica/alumina ratio (Si:Al) of less than 5 while the second molecular sieve has a silica/alumina ratio of greater than 5. Additionally or alternatively, one molecular sieve may have a pore size of at least about 6 Angstroms and/or the second molecular sieve may have a pore size of less than about 6 Angstroms.

In various embodiments, the treated benzene stream contains: (i) less than 3.0 ppm of sulfur, or less than 1.0 ppm, of sulfur or less than 0.3 ppm of sulfur; and/or (iii) less than 3.0 ppm of nitrogen, or less than 1.0 ppm of nitrogen, or less than 0.3 ppm of nitrogen.

It will be understood that the hydrogen and benzene treatments disclosed herein may be performed separately or in conjunction with one or more hydroalkylation processes.

Hydroalkylation

As discussed above, the hydroalkylation process includes contacting (e.g., hydroalkylating) benzene with hydrogen to produce CHB:

Conveniently, the total feed to the hydroalkylation step contains less than 500 ppm, or less than 100 ppm, or about 12-20 ppm of water.

The hydroalkylation reaction can be conducted in a wide range of reactor configurations including fixed bed, slurry reactors, and/or catalytic distillation towers. In addition, the reaction can be conducted in a single reaction zone or in a plurality of reaction zones, in which one or more of the hydrogen and benzene reactant streams are introduced to the reaction in stages. In one embodiment, hydrogen addition or benzene addition can be staged with internal recycle for cooling.

Suitable hydroalkylation conditions include reaction temperatures between about 100° C. and about 400° C., such as between about 125° C. and about 250° C., while suitable reaction pressures are between about 100 and about 7,000 kPa, gauge such as between about 500 and about 5,000 kPa, gauge. Suitable values for the molar ratio of hydrogen to benzene are between about 0.15:1 and about 15:1, such as between about 0.4:1 and about 4:1 for example between about 0.4 and about 0.9:1.

The hydroalkylation may be conducted in the presence or absence of a hydroalkylation catalyst. The hydroalkylation catalyst may be a bifunctional catalyst comprising a molecular sieve of the MCM-22 family and a hydrogenation metal.

Molecular sieves of MCM-22 family are described, for example, in PCT Application No. PCT/US2008/072843 filed on Aug. 12, 2008, which is hereby incorporated by reference for this purpose. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) EMM-10; (b) EMM-11; (c) EMM-12; (d) EMM-13; (e) MCM-49; (f) MCM-56; and (g) isotypes of MCM-49 and MCM-56, such as ITQ-2. Other molecular sieves, such as zeolite beta, are also contemplated.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 and about 10 wt %, such as between about 0.1 and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

In various embodiments, the molecular sieve and the hydrogenation metal are coextruded. The hydrogenation metal may also be directly supported on the molecular sieve by, for example, impregnation or ion exchange. In one embodiment, at least 50 wt %, for example at least 75 wt %, and generally substantially all of the hydrogenation metal is supported on an inorganic oxide separate from but composited with the molecular sieve. In one embodiment, the hydrogenation metal is supported on an inorganic oxide.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13 and 14 of the Periodic Table of Elements, such as alumina, titania, and/or zirconia. As used herein, the numbering scheme for the Periodic Table Groups is as disclosed in Chemical and Engineering News, 63(5), p. 27 (1985).

The hydrogenation metal may be deposited on the inorganic oxide, conveniently by impregnation, before the metal-containing inorganic oxide is composited with the molecular sieve. Typically, the catalyst composite is produced by co-pelletization, in which a mixture of the molecular sieve and the metal-containing inorganic oxide are formed into pellets at high pressure (generally about 350 to about 350,000 kPa), or by co-extrusion, in which a paste of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Although the hydroalkylation step is highly selective towards cyclohexylbenzene, the effluent from the hydroalkylation reaction will normally contain some dialkylated products, as well as unreacted benzene and the desired monoalkylated species. The unreacted benzene is normally recovered by distillation and recycled to the alkylation reactor. The bottoms from the benzene distillation are further distilled to separate the monocyclohexylbenzene product from any dicyclohexylbenzene and other heavies. Depending on the amount of dicyclohexylbenzene present in the reaction effluent, it may be desirable to either (a) transalkylate the dicyclohexylbenzene with additional benzene or (b) dealkylate the dicyclohexylbenzene to maximize the production of the desired monoalkylated species.

Transalkylation with additional benzene is typically effected in a transalkylation reactor separate from the hydroalkylation reactor over a suitable transalkylation catalyst, such as a molecular sieve of the MCM-22 family, zeolite beta, MCM-68 (see U.S. Pat. No. 6,014,018) and zeolite Y. The transalkylation reaction is typically conducted under at least partial liquid phase conditions, which suitably include a temperature of about 100 to about 300° C., a pressure of about 800 to about 3500 kPa, a weight hourly space velocity of about 1 to about 10 hr$^{-1}$ on total feed.

In accordance with various aspects of the present invention, the hydroalkylation processes disclosed herein may be conducted alone, or in conjunction with one or more steps of a process to produce phenol, such as: (i) oxidation; (ii) cleavage; and/or (iii) dehydrogenation.

Oxidation

As discussed above, the hydroalkylation processes described herein may be conducted as part of a process that includes oxidation of at least a portion of the cyclohexylbenzene produced during hydroalkylation to produce at least some cyclohexylbenzene hydroperoxide.

Oxidation may be accomplished by introducing an oxygen-containing gas, such as air or enriched air into a liquid phase. The oxidation may be conducted in the presence or absence of an oxidation catalyst.

Suitable oxidation catalysts for the oxidation step are the N-hydroxy substituted cyclic imides described in U.S. Pat. No. 6,720,462 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy (pyromellitic diimide), N,N'-dihydroxy(benzophenone-3,3', 4,4'-tetracarboxylic diimide), N-hydroxymaleimide, pyridine-2,3-dicarboximide, N-hydroxysuccinimide, N-hydroxy (tartaric imide), N-hydroxy-5-norbornene-2,3-dicarboximide, exo-N-hydroxy-7-oxabicyclo[2.2.1]hept-5-ene-2,3-dicarboximide,N-hydroxy-cis-cyclohexane-1,2-dicarboximide, N-hydroxy-cis-4-cyclohexene-1, 2dicarboximide, N-hydroxynaphthalimide sodium salt or N-hydroxy-o-benzenedisulphonimide.

These materials can be used either alone or in the presence of a free radical initiator and can be used as liquid-phase, homogeneous catalysts or can be supported on a solid carrier to provide a heterogeneous catalyst. Typically, the N-hydroxy substituted cyclic imide or the N,N',N'''-trihydroxyisocyanuric acid is employed in an amount between about 0.0001 wt % to about 15 wt %, such as between about 0.001 to about 5 wt %, of the CHB.

Suitable oxidation conditions include a temperature between about 70° C. and about 200° C., such as about 90° C. to about 130° C., and a pressure of about 50 to about 10,000 kPa. Any oxygen-containing gas, preferably air, can be used as the oxidizing medium. The reaction can take place in batch reactors or continuous flow reactors. In one embodiment, the acids generated during oxidation are in the off gas streams and are neutralized with caustic (e.g., sodium carbonate) and separated or eliminated with the use of equipment such as chillers, decanter drums and adsorbers. The aqueous effluent from the oxidizers may then be neutralized and sent to waste water.

Cleavage

The hydroalkylation process may be conducted as part of a process that includes cleavage of at least a portion of the cyclohexylbenzene hydroperoxide that is produced during oxidation to produce at least some phenol and cyclohexanone.

Cleavage of the cyclohexylbenzene hydroperoxide can be effected by contacting the hydroperoxide with a catalyst in the liquid phase at a temperature of about 20° C. to about 150° C., such as about 40° C. to about 120° C., a pressure of about 50 to about 2,500 kPa, such as about 100 to about 1000 kPa. The hydroperoxide is preferably diluted in an organic solvent inert to the cleavage reaction, such as methyl ethyl ketone (MEK), cyclohexanone, phenol or CHB, to assist in heat removal. The cleavage reaction is conveniently conducted in a series of heat exchangers, one or more well mixed reaction vessels, or a catalytic distillation unit.

The catalyst employed in the cleavage step can be a homogeneous catalyst or a heterogeneous catalyst. Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid, with preferred concentrations in the range of about 0.01 to about 2.0 wt %, or about 0.05 to about 0.5 wt % based upon total weight of the solution in the cleavage reactor. For a homogeneous acid catalyst, a neutralization step preferably follows the cleavage step. Such a neutralization step typically involves contact with a basic component, with subsequent decanting of a salt-enriched aqueous phase.

Any suitable heterogeneous catalyst may be used, such as those described in U.S. Pat. No. 4,870,217, which is incorporated by reference for this purpose.

Dehydrogenation

The hydroalkylation processes described herein may be conducted as part of a process that includes dehydrogenation of at least a portion of the cyclohexanone that is made during the production of phenol. Dehydrogenation generally involves contacting the cyclohexanone with a dehydrogenation catalyst.

The dehydrogenation catalyst may comprise: (i) a support; (ii) a first component; and (iii) a hydrogenable component produced such that the catalyst exhibits an oxygen chemisorption of greater than 0.5, preferably greater than 0.6 and more preferably greater than 0.7. Chemisorption measurements are obtained under static high vacuum conditions on a Quantachrome Autosorb 1A instrument. Approximately 0.3-0.5 grams of catalyst are loaded into a quartz cell and dried in flowing He by heating at 4° C./min to 130° C. and holding for 1 hour. The flow is then switched to hydrogen and the catalyst is reduced in flowing hydrogen by heating at 2° C./min to 425° C., holding isothermal for 2 hours, and then cooling to 400° C. in flowing hydrogen. Following reduction, the sample is evacuated (while still at 400° C.) with a turbomolecular pump for 30 minutes to remove any chemisorbed hydrogen. With the sample still under vacuum, the temperature is lowered to 40° C. and held isothermal during subsequent experiments. An 8-point isotherm (with pressures between 80 and 400 torr [10.7 to 53.3 kPa]) is measured at 40° C. with O2 as the adsorbent molecule. Extrapolation of the linear portion of this curve to zero pressure gives the total or combined adsorption uptake.

Conveniently, the support employed in the dehydrogenation catalyst is selected from the group consisting of silica, a silicate, an aluminosilicate such as including zeolites and MCM-41, zirconia, carbon and carbon nanotubes, and preferably comprises silica. Impurities which can be present in the catalyst support (e.g., silica) are, for example, sodium salts such as sodium silicate which can be present from anywhere from about 0.01 to about 2 wt %.

Generally, the first component employed in the present catalyst comprises at least one metal selected from Groups 6 to 10 of the Periodic Table of Elements and compounds and mixtures thereof, such as platinum, palladium and compounds and mixtures thereof. In another embodiment, the first component comprises at least one metal selected from Group 10 of the Periodic Table of Elements and compounds and mixtures thereof. Typically, the first component is present in an amount between about 0.1 and about 10 wt % of the catalyst.

In addition, the catalyst comprises a second component comprising at least one metal or compound thereof selected from Group 1 and Group 2 of the Periodic Table of Elements wherein, said at least one metal or compound thereof selected from Group 1 and Group 2 of the Periodic Table of Elements is present in an amount of at least 0.1 wt %, at least 0.2 wt %, at least 0.3 wt %, at least 0.4 wt % and at least 0.5 wt %. In one embodiment, the second component comprises at least one metal or compound thereof selected from Group 1 of the Periodic Table of Elements, such as potassium, cesium and rubidium and compounds and mixtures thereof; preferably potassium and potassium compounds. In another embodiment, the second component comprises at least one metal or compound thereof selected from Group 1 or 2 of the Periodic Table of Elements. Typically, the second component is present in an amount between about 0.1 and about 5 wt % of the catalyst.

Suitable dehydrogenation conditions include a temperature of about 250° C. to about 750° C., a pressure of about atmospheric to about 500 psi-gauge (psig) [100 to 3447 kPa-gauge (kPa,g)], a weight hourly space velocity of about 0.2 to about 50 hr$^{-1}$, and a hydrogen to cyclohexanone-containing feed molar ratio of about 0 to about 20.

The temperature of the dehydrogenation process may be from about 300° C. to about 750° C. and from about 400° C. to about 500° C.

The pressure of the dehydrogenation process may be from about 0 to about 300 psig (0 to 2.07 MPa,g) or from about 100 to about 300 psig (0.69 to 2.07 MPa,g).

The reactor configuration used for the dehydrogenation process generally comprises one or more fixed bed reactors containing a solid catalyst with a dehydrogenation function.

In one embodiment, separation can be enhanced by conducting the distillation under at least partial vacuum, typically at below 101 kPa. Moreover, extractive distillation processes are known. See for example, U.S. Pat. Nos. 4,021,490; 4,019,965; 4,115,207; 4,115,204; 4,115,206; 4,201,632; 4,230,638; 4,167,456; 4,115,205; and 4,016,049.

In another embodiment, the cleavage effluent is subjected to one or more separation processes to recover or remove one or more components of the effluent prior to dehydrogenation. In particular, the cleavage effluent is conveniently subjected to at least a first separation step to recover some or all of the phenol from the effluent, typically so that the effluent stream fed to said dehydrogenation reaction contains less than 50 wt %, for example less than 30 wt %, such as less than 1 wt %, phenol. The first separation step is conveniently effected by vacuum distillation and the same, or additional vacuum distillation steps, can be used to remove components boiling below 155° C. (as measured at 101 kPa), such as benzene and cyclohexene, and/or components boiling above 185° C. (as measured at 101 kPa), such as 2-phenyl phenol and diphenyl ether, prior to feeding the effluent stream to the dehydrogenation reaction.

Figure 5:
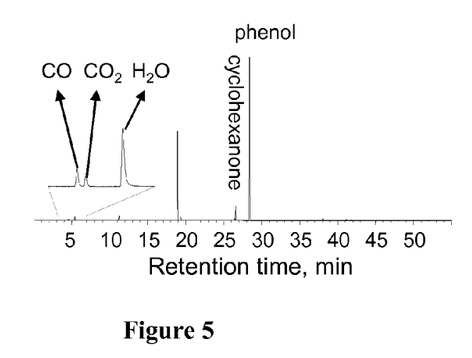
FIG. 5 is a chromatograph of a hydrogen stream taken from a dehydrogenation reaction.

In various exemplary embodiments, the hydrogen formed during dehydrogenation may be recycled to the hydroalkylation step, or optionally, the hydrogen treatment step prior to oxidation. Recycle to the hydrogen treatment step is particularly advantageous because, as illustrated in FIG. 5 (with reference to Example 5), it has been discovered that carbon monoxide and carbon dioxide in the hydrogen stream is formed in dehydrogenation step (e.g., during cyclohexanone decarboxylation reaction). As previously discussed, carbon monoxide and carbon dioxide compounds can be detrimental to the hydroalkylation process.

By employing the dehydrogenation process discussed herein, substantially all the cyclohexanone can be converted to phenol. This can readily be achieved by, for example, contacting the phenol with hydrogen in the presence of a hydrogenation catalyst, such as platinum or palladium, under conditions including a temperature of about 20° C. to about 250° C., a pressure of about 101 kPa, gauge to about 10000 kPa, gauge and a hydrogen to phenol molar ratio of about 1:1 to about 100:1.

Exemplary Processes

Figure 6:
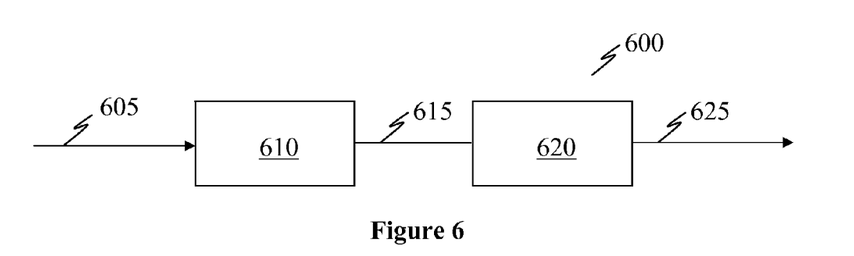
FIG. 6 illustrates an exemplary hydroalkylation process.

FIG. 6 illustrates hydroalkylation process 600 comprising Step 610: treating hydrogen stream 605 to at least partially remove an impurity and form stream 615; and Step 620: hydroalkylating stream 615 with benzene in the presence of an hydroalkylation catalyst under hydroalkylation conditions to form composition 625 comprising at least some cyclohexylbenzene.

Figure 7:
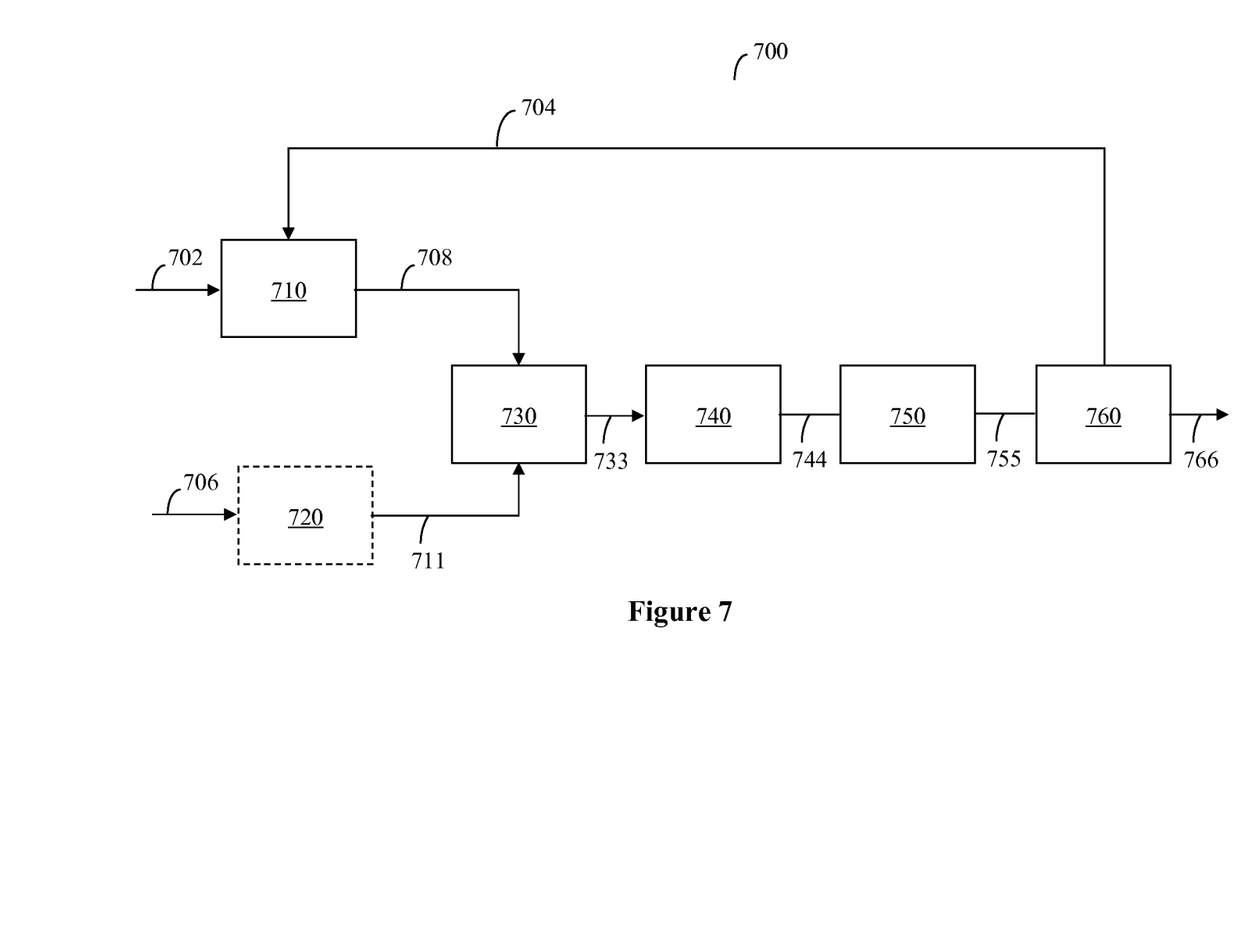
FIG. 7 illustrates an embodiment of a process for producing phenol comprising recycle of a hydrogen stream to the hydroalkylation process.

In the embodiment illustrated in FIG. 7, phenol process 700 comprises: Step 710: treating hydrogen stream 702 and recycle stream 704 to at least partially remove at least one impurity and form stream 708; optional Step 720: treating benzene stream 706 to at least partially remove at least one impurity to form stream 711; Step 730: hydroalkylating streams 708 and 711 to form at least some cyclohexylbenzene in stream 733; Step 740: oxidizing at least a portion of the cyclohexylbenzene in stream 733 to form cyclohexylbenzene peroxide in stream 744; Step 750: cleaving the cyclohexylbenzene peroxide in stream 744 to form at least some phenol and cyclohexanone in stream 755; and Step 760: dehydrogenating at least a portion of the cyclohexanone in stream 755 to form at least some additional phenol in stream 766 and at least some hydrogen in recycle stream 704.

The invention will now be more particularly described with reference to the following non-limiting Examples and the accompanying figures.

Example 1

Catalyst Performance with Purified and Carbon Monoxide-Spiked Hydrogen Stream

This Example illustrates the deleterious effect of carbon monoxide in the hydrogen stream on the performance of a hydroalkylation catalyst.

A palladium (Pd)/MCM-49 hydroalkylation catalyst was prepared by depositing 0.6 wt % of palladium nitrate onto an alumina support to form a Pd/Al$_2$O$_3$ compound. The Pd/Al$_2$O$_3$ compound was then coextruded with an MCM-49 molecular sieve and a pseudo-boehmite binder. The ratio of Pd/Al$_2$O$_3$/MCM-49/pseudo-boehmite binder was 42:42:18. The mixture was then calcined at 538° C. to dry the mixture and convert the pseudo-boehmite to gamma alumina.

The highly purified hydrogen stream used in Example 1 was 99.999% pure. The highly purified benzene stream was purchased from Aldrich Chemical Company at 99.9% purity and was further purified to be 99.999% pure through treatment with various molecular sieves (namely, 13X, 4A, clay, activated alumina and MCM-49). Hydroalkylation conditions were maintained at a temperature of about 145° C. and a pressure of about 165 psig (1.14 MPa, gauge) throughout the experiment. The ratio of hydrogen to benzene was 0.65.

Days 0-20, the highly purified hydrogen and highly purified benzene streams were hydroalkylated in a downflow reactor at 3.5 hr$^{-1}$ weight hourly space velocity (WHSV). As illustrated in FIG. 1, the benzene and hydrogen conversions were initially about 28% and 70%, respectively and then stabilized at about 27% and 57%, respectively.

Days 20-22: highly purified hydrogen and highly purified benzene streams were hydroalkylated under the same conditions, except the WHSV was decreased to 3.0 hr$^{-1}$ to increase conversion. As illustrated in FIG. 1, benzene and hydrogen conversion were maintained at about 30% and 64%, respectively.

Days 22-24: the highly purified hydrogen stream was spiked with 1.3 ppm of carbon monoxide and hydroalklyated with the highly purified benzene stream. As shown in FIG. 1, benzene and hydrogen conversion decreased to about 22% and 45%, respectively.

Days 24-30: the spiked hydrogen stream was replaced with the highly purified hydrogen and hydroalkyklated with the highly purified benzene stream at 3 hr$^{-1}$ WHSV. As shown in FIG. 1, conversion rapidly recovered once the carbon monoxide-spiked hydrogen feed was removed.

Example 2

Catalyst Performance with Purified and Hydrogen Sulfide-Spiked Hydrogen Feed

The catalyst, highly purified hydrogen and benzene streams and hydroalkylation conditions in this Example are the same as in Example 1.

Days 0-12: highly purified hydrogen was reacted (i.e., hydroalkylated) with highly purified benzene in the presence of a Pd/MCM-49 catalyst at a WHSV of 3.5 hr$^{-1}$. As shown in FIG. 2, benzene and hydrogen conversion were initially about 16% and 33%, respectively and then stabilized at about 29% and 62%, respectively.

Days 12-15: The purified hydrogen feed was replaced with a hydrogen feed spiked with 64 ppm hydrogen sulfide (H$_2$S) and hydroalkylated with the purified benzene stream. As shown in FIG. 2, the catalyst lost essentially all of its activity in 2-3 days.

Example 3

Catalyst Performance with Purified and Diphenylsulfide-Spiked Benzene Stream

This Example illustrates the effect of sulfur compounds in the benzene stream on the performance of a Pd/MCM-49 hydroalkylation catalyst. The Pd/MCM-49 was prepared in the same manner as Example 1. The hydroalkylation conditions were also the same as in Example 1.

Two different benzene streams were hydroalkylated. The first benzene stream comprised 99.9% pure benzene feed purchased from Aldrich Chemical Company and was treated with various molecular sieves (i.e., 13X, 4A, clay, activated alumina and MCM-49) to become highly purified (about 99.999% pure). The second benzene stream comprised 99.9% pure benzene feed purchased from Aldrich Chemical Company and was spiked with 5 ppm diphenylsulfide (DPS) in order to study the potential effect of sulfur compounds on the Pd/MCM-49 hydroalkylation catalyst.

Days 0-19: the first benzene stream (i.e., the highly purified benzene stream) was hydroalkylated at 3.5 hr$^{-1}$ WHSV. As shown in FIG. 3, benzene and hydrogen conversions were initially about 28% and 70%, respectively and then stabilized to about 27% and 57% respectively.

Days 20-29: the WHSV was decreased to 3.0 hr WHSV to increase conversion. The average benzene and hydrogen conversions increased to about 30% and 63%, respectively.

On Day 30: the first benzene stream was replaced with the second benzene stream. As seen in FIG. 3, conversion of benzene and hydrogen dropped to nearly 0% in 1-2 days.

Example 4

Extended Run Using a Purified Benzene Stream

FIG. 4 illustrates catalyst stability during hydroalkylation with highly purified benzene and hydrogen streams.

The catalyst and highly purified benzene and hydrogen streams were prepared in the same manner as the first benzene stream in Example 1. The hydroalkylation conditions were also the same as Example 1. The benzene stream was hydroalkylated at 3.5 hr$^{-1}$ WHSV for forty (43) days.

As shown in FIG. 4, after initial ramp-up, benzene and hydrogen conversion were stable at about 31% and 65%, respectively. Excellent catalyst stability was maintained until Day 43, when the experiment was terminated voluntarily.

Example 5

CO$_x$ Content in Hydrogen Stream after Dehydrogenation

Cyclohexanone was dehydrogenated using a catalyst comprising 1 wt % platinum, 1 wt % potassium, and a silica support at 425° C. and 100 psig (689 KPa, gauge). The WHSV was 3.75 hr$^{-1}$ and the hydrogen/cyclohexanone ratio was 2. As shown in the ion chromatograph in FIG. 5, the carbon monoxide and carbon dioxide peaks are clearly visible. The concentration of carbon monoxide and carbon dioxide in the hydrogen stream is estimated to be about 100 ppm to about 5,000 ppm.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

Additionally or alternately, the invention can be described by the following embodiments:
1. A hydroalkylation process comprising:
   (a) treating a hydrogen stream comprising hydrogen and an impurity, wherein the treating reduces the amount of the impurity in the hydrogen stream; and
   (b) contacting benzene with the hydrogen to form at least some cyclohexylbenzene.

2. The process of embodiment 1, wherein the impurity is one or more of carbon monoxide and carbon dioxide.

3. The process of embodiment 2, wherein the treating (a) comprises contacting the hydrogen stream with a methanation catalyst under methanation conditions to convert at least a portion of the impurity and the hydrogen to methane and water.

4. The process of embodiment 3, wherein the methanation catalyst comprises at least one Group 8-10 metal and a support.

5. The process of embodiment 3, wherein the methanation catalyst comprises nickel and a support.

6. The process of embodiment 5, wherein the support comprises one or more of aluminum oxide, silica, silicate and aluminosilicate.

7. The process of embodiment 3, wherein the methanation conditions comprise a temperature of about 200° C. to about 500° C. and a pressure of about 0.1 MPa, gauge to about 2.0 MPa, gauge.

8. The process of embodiment 1, wherein the impurity is one or more of hydrogen sulfide, diphenylsulfide and carbonyl sulfide.

9. The process of embodiment 8, wherein the treating (a) comprises scrubbing the hydrogen stream with an amine to at least partially remove the impurity.

10. The process of embodiment 9, wherein the amine is one or more of monoethanolamine, diethanolamine, triethanolamine, methylamine, dimethylamine and trimethylamine.

11. The process of embodiment 8, wherein the treating (a) comprises scrubbing the hydrogen stream with a caustic.

12. The process of embodiment 11, wherein the caustic is one or more of sodium hydroxide and potassium hydroxide.

13. The process of embodiment 8, wherein the treating (a) comprises contacting the hydrogen stream with an adsorbent.

14. The process of embodiment 13, wherein the adsorbent is one or more of activated alumina, zinc and a copper/zinc compound.

15. The process of embodiment 1, wherein the contacting (b) is conducted in the presence of a hydroalkylation catalyst comprising a molecular sieve and a hydrogenation metal.

16. The process of embodiment 15, wherein the molecular sieve and hydrogenation metal are co-extruded.

17. The process of embodiment 15, wherein the molecular sieve is one or more of MCM-22, MCM-49, and MCM-56 and zeolite B.

18. The process of embodiment 15, wherein the hydrogenation metal comprises one or more of palladium, cobalt and nickel.

19. The process of embodiment 1, wherein the treating (a) reduces the amount of the impurity in the hydrogen stream to about 50 ppm or less.

20. The process of embodiment 1, wherein the treating (a) reduces the amount of the impurity in the hydrogen stream to about 5 ppm or less.

21. The process of embodiment 1, wherein the treating step (a) reduces the amount of the impurity in the hydrogen stream to about 0.5 ppm or less.

22. The process of embodiment 1, further comprising pretreating the benzene prior to the contacting (b) to at least partially remove a second impurity.

23. The process of embodiment 22, wherein the second impurity is one or more of nitrogen and a sulfur compound.

24. The process of embodiment 22, wherein the pretreating comprises contacting the benzene with an adsorbent.

25. The process of embodiment 24, wherein the adsorbent comprises one or more molecular sieves selected from 3A, 4A, 5A, clay, activated alumina, amorphous silica-alumina and zeolite.

26. The process of embodiment 24, wherein the adsorbent comprises at least a first silica-alumina molecular sieve and a second silica-alumina molecular sieve, wherein the first silica-alumina molecular sieve has a silica/alumina molar ratio of less than 5 and the second silica-alumina molecular sieve has a silica/alumina molar ratio of greater than 5.

27. The process of embodiment 24, wherein the adsorbent comprises at least a first molecular sieve and a second molecular sieve, wherein the first molecular sieve has an average pore size of at least 6 Angstroms and the second molecular sieve has an average pore size of less than 6 Angstroms.

28. The process of embodiment 1, further comprising:
(c) oxidizing at least a portion of the cyclohexylbenzene to form at least some cyclohexylbenzene hydroperoxide.

29. The process of embodiment 28, further comprising:
(d) cleaving at least a portion of the cyclohexylbenzene hydroperoxide to form at least some phenol and cyclohexanone.

30. The process of embodiment 29, further comprising:
(e) dehydrogenating at least a portion of the cyclohexanone to form at least some phenol and hydrogen.

31. The process of embodiment 30, further comprising:
(f) recycling at least a portion of the hydrogen formed in the dehydrogenating; and
(e) to the hydrogen stream in the treating (a).

32. A hydroalkylation process comprising:
(a) treating a hydrogen stream comprising hydrogen and an impurity, wherein the treating reduces the amount of the impurity in the hydrogen stream, wherein the treating (a) comprises one or more of:
(i) contacting the hydrogen stream with a methanation catalyst under methanation conditions to convert at least some of the impurity and the hydrogen to methane and water;
(ii) scrubbing the hydrogen stream with one or more of an amine and a caustic; and
(iii) contacting the hydrogen stream with an adsorbent; and
(b) contacting benzene with the hydrogen in the presence of a hydroalkylation catalyst to form at least some cyclohexylbenzene.

33. A hydroalkylation process comprising:
(a) contacting a benzene stream comprising benzene and an impurity with an adsorbent, wherein the contacting reduces the amount of the impurity in the benzene stream; and
(b) contacting the benzene with hydrogen to form at least some cyclohexylbenzene.

34. The hydroalklyation process of embodiment 33, wherein the adsorbent comprises one or more of 3A, 4A, 5A, clay, activated alumina and zeolite.

35. The hydroalkylation process of embodiment 34, wherein the adsorbent comprises at least a first molecular sieve and a second molecular sieve, wherein the first molecular sieve has an average pore size of at least 6 Angstroms and the second molecular sieve has an average pore size of less than 6 Angstroms.

36. The hydroalkylation process of embodiment 33, wherein the adsorbent comprises a first alumina-silica molecular sieve and a second alumina-silica molecular sieve, wherein the first alumina-silica molecular sieve has a silica/alumina ratio of greater than about 5 and the second alumina-silica molecular sieve has a silica/alumina ratio of less than about 5.

The invention claimed is:

1. A hydroalkylation process comprising:
   (a) treating a hydrogen stream comprising hydrogen and an impurity having the general formula $CO_x$, wherein the treating (a) reduces the amount of the impurity to about 0.1 ppm or less in the hydrogen stream;
   (b) pretreating a benzene stream comprising benzene and a benzene impurity to remove the benzene impurity in the benzene stream to about 0.1 ppm or less; and
   (c) contacting the pretreated benzene stream with the treated hydrogen stream in the presence of a hydroalkylation catalyst to form cyclohexylbenzene;
   wherein the hydroalkylation catalyst comprises a molecular sieve selected from the group consisting of MCM-22, EMM-10, EMM-11, EMM-12, EMM-13, MCM-49, MCM-56, isotypes of MCM-49 and MCM-56, and any combination thereof.

2. The process of claim 1, wherein the impurity is one or more of carbon monoxide and carbon dioxide.

3. The process of claim 2, wherein the treating (a) comprises contacting the hydrogen stream with a methanation catalyst under methanation conditions to convert a portion of or all of the impurity and the hydrogen to methane and water.

4. The process of claim 3, wherein the methanation catalyst comprises at least one Group 8-10 metal and a support.

5. The process of claim 3, wherein the methanation catalyst comprises nickel and a support.

6. The process of claim 5, wherein the support comprises one or more of aluminum oxide, silica, silicate and aluminosilicate.

7. The process of claim 3, wherein the methanation conditions comprise a temperature of about 200° C. to about 500° C. and a pressure of about 0.1 MPa, gauge to about 2.0 MPa, gauge.

8. The process of claim 1, wherein the hydrogen stream further comprises a second impurity selected from the group consisting of hydrogen sulfide, diphenylsulfide, carbonyl sulfide, and any combination thereof; and wherein the treating (a) further reduces the amount of the second impurity to about 100 ppm or less.

9. The process of claim 8, wherein the treating (a) comprises scrubbing the hydrogen stream with an amine to at least partially remove the second impurity.

10. The process of claim 9, wherein the amine is one or more of monoethanolamine, diethanolamine, triethanolamine, methylamine, dimethylamine and trimethylamine.

11. The process of claim 8, wherein the treating (a) comprises scrubbing the hydrogen stream with a caustic.

12. The process of claim 11, wherein the caustic is one or more of sodium hydroxide and potassium hydroxide.

13. The process of claim 8, wherein the treating (a) comprises contacting the hydrogen stream with an adsorbent.

14. The process of claim 13, wherein the adsorbent is one or more of activated alumina, zinc and a copper/zinc compound.

15. The process of claim 1, wherein the contacting (c) is conducted in the presence of a hydroalkylation catalyst comprising a molecular sieve and a hydrogenation metal.

16. The process of claim 15, wherein the hydrogenation metal comprises one or more of palladium, cobalt and nickel.

17. The process of claim 1, wherein the treating (a) reduces the amount of the impurity in the hydrogen stream to about 0.01 ppm or less.

18. The process of claim 1, wherein the benzene impurity is nitrogen.

19. The process of claim 1, wherein the pretreating comprises contacting the benzene with an adsorbent.

20. The process of claim 19, wherein the adsorbent comprises at least a first silica-alumina molecular sieve and a second silica-alumina molecular sieve, wherein the first silica-alumina molecular sieve has a silica/alumina molar ratio of less than 5 and the second silica-alumina molecular sieve has a silica/alumina molar ratio of greater than 5.

21. The process of claim 1, further comprising:
   (d) oxidizing a portion or all of the cyclohexylbenzene to form cyclohexylbenzene hydroperoxide;
   (e) cleaving a portion or all of the cyclohexylbenzene hydroperoxide to form phenol and cyclohexanone;
   (f) dehydrogenating a portion or all of the cyclohexanone to form phenol and hydrogen; and
   (g) recycling a portion or all of the hydrogen formed during dehydrogenation to the hydrogen stream at a point prior to the treating (a) such that the hydrogen stream comprises the portion or all of the hydrogen formed during dehydrogenation.

22. The process of claim 21, wherein the treating (a) reduces the amount of the impurity in the hydrogen stream, to about 0.01 ppm or less.

23. A hydroalkylation process comprising:
   (a) treating a hydrogen stream comprising hydrogen, a first impurity having the general formula $CO_x$, and a second impurity comprising one or more sulfur-containing compounds,
   wherein the treating (a) reduces the amount of the first impurity in the hydrogen stream to less than 0.1 ppm,
   wherein the treating (a) comprises contacting the first impurity with a methanation catalyst under methanation conditions to convert some or all of the first impurity and a portion of the hydrogen to methane and water,
   wherein the treating (a) further comprises one or more of:
      i) contacting the hydrogen stream with one or more of an amine and a caustic; and
      ii) contacting the hydrogen stream with an adsorbent;
   (b) pretreating a benzene stream comprising benzene and a benzene impurity to remove the benzene impurity in the benzene stream to about 0.1 ppm or less; and
   (c) contacting the pretreated benzene stream with the treated hydrogen stream in the presence of a hydroalkylation catalyst to form at least some cyclohexylbenzene;
   wherein the hydroalkylation catalyst comprises a molecular sieve selected from the group consisting of MCM-22, EMM-10, EMM-11, EMM-12, EMM-13, MCM-49, MCM-56, isotypes of MCM-49 and MCM-56, and any combination of the foregoing.

24. The process of claim 18, wherein pretreating the benzene reduces the amount of the benzene impurity in the benzene to about 0.01 ppm or less.

* * * * *